United States Patent [19]
Giannella et al.

[11] Patent Number: 5,281,136
[45] Date of Patent: Jan. 25, 1994

[54] SUPPORT AND GUIDE APPARATUS FOR A DENTAL DRILL

[75] Inventors: Gianni M. Giannella, Turin; Giuseppe Gava, Via Italia 18, Settimo, both of Italy

[73] Assignee: Giuseppe Gava, Settimo Torinese, Italy

[21] Appl. No.: 893,405

[22] Filed: Jun. 3, 1992

[30] Foreign Application Priority Data

Jun. 4, 1991 [IT] Italy ................ TO.91-A/000420
Jun. 4, 1991 [IT] Italy ................ TO.91-A/000421

[51] Int. Cl.$^5$ ........................... A61C 3/02; A61C 1/02
[52] U.S. Cl. ........................................ 433/76; 433/109
[58] Field of Search ................... 433/75, 76, 108, 109

[56] References Cited

U.S. PATENT DOCUMENTS

| | | | |
|---|---|---|---|
| 930,082 | 8/1909 | Pieper | 433/109 |
| 2,801,469 | 6/1957 | Solle . | |
| 2,833,038 | 5/1958 | Gladstone et al. | 433/109 |
| 2,873,527 | 2/1959 | Flatland | 433/109 |
| 3,083,462 | 2/1963 | Jermyn . | |
| 5,017,139 | 5/1991 | Mushabac | 433/108 X |

FOREIGN PATENT DOCUMENTS 3500921 7/1986 Fed. Rep. of Germany .
2166240 8/1973 France .

*Primary Examiner*—John J. Wilson
*Assistant Examiner*—Nicholas D. Lucchesi
*Attorney, Agent, or Firm*—Merchant & Gould, Smith, Edell, Welter & Schmidt

[57] ABSTRACT

Support and guide apparatus (1) for a dental drill (2) comprises an articulated arm (3) which can be attached to a fixed support member (4) and provided with an attachment member (88) for a tail (20) of the drill (2); the arm (3) is provided with a device (70) which acts to maintain the axis of rotation (A) of the drill turbine orthogonal to a predetermined working plane ($\tau$) and a counterweight (108) which balances the weight of the movable parts in any position of the arm itself.

The apparatus (1) further includes stabilization apparatus (201) for the head (203) and jaw (205) comprising a side bracket (241) lockable with respect to the headrest of a dental chair, which (241) carries a transverse element (246) projecting therefrom to maintain the patient's jaw in the open position.

11 Claims, 7 Drawing Sheets

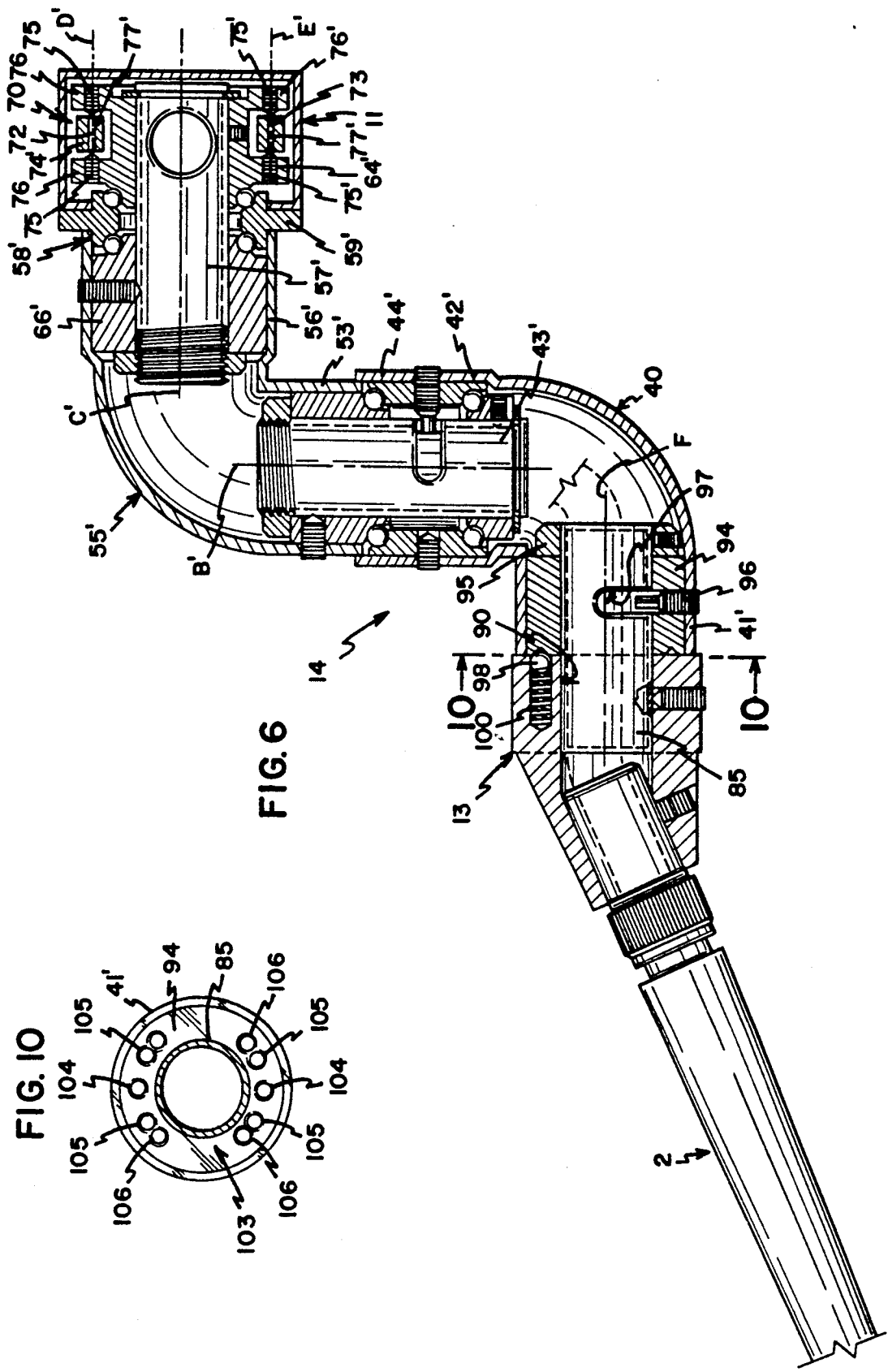

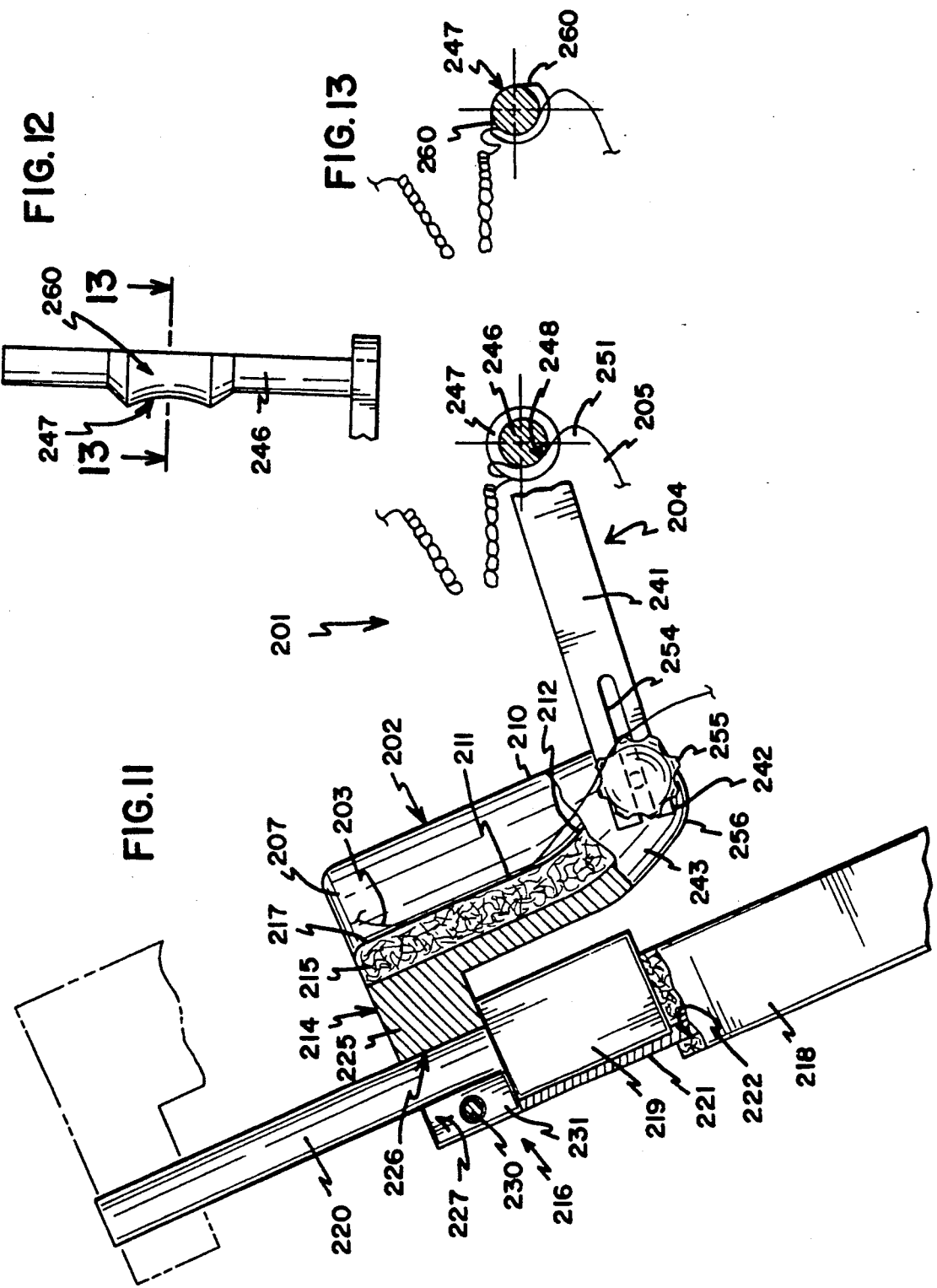

SUPPORT AND GUIDE APPARATUS FOR A DENTAL DRILL

The present invention relates to a support and guide apparatus for a dental drill, particularly adapted for undertaking the operations performed in preparation for a prosthesis.

As is known, preparation for a prosthesis comprises the volumetric reduction of a tooth in the axial and perimetral directions to allow it to be covered, for the purpose of reinstating the original shape and functionality of the tooth, and possibly for utilising the covered tooth as a support for anchoring prosthetic elements in replacement of lost teeth.

The preparation is effected by means of a high speed turbine drill by reducing the crown of the tooth to a conical stump; the requirements which such preparation must satisfy are essentially as follows:

sufficient degree of volumetric reduction to ensure an adequate thickness and therefore mechanical strength of the reconstruction material;

an optimum cone angle and height to ensure a good retention and stability of the prosthesis;

absence of undercuts for easy insertion and extraction of the prosthesis.

Preparation for a prosthesis is normally effected by guiding the drill freehand; the correct inclination of the side walls of the stump is obtained with the use of a milling cutter having an optimum cone angle (typically about 6°).

From what has been mentioned above it will be evident that the traditional technique in preparation for a prosthesis is a rather critical operation.

In fact, as well as the objective difficulties associated with the nature of the operating field (poor visibility, restricted space, movement of the patient) there are subjective components in relation to the operator (tremors, tiredness, stress) which, in consideration of the high precision which is required, make preparation for prostheses with characteristics close to the ideal very problematical. It is evident, for example, that an involuntary inclination of the axis of the milling cutter through a few degrees, an inclination which is difficult for the operator to appreciate, is enough to form a stump with excessively inclined walls (which will result in a poor retention of the prosthesis) or an insufficient inclination, or even an undercut which would prevent the correct insertion of the prosthesis.

The difficulties are further increased, in an exponential manner, with the number of stumps which must be prepared, for example in the case of protheses having two or more supports (bridges); in this case, in fact, as well as "absolute" errors in the preparation of the individual teeth, relative errors must also be taken into consideration (for example relative inclination between the insertion axis of the individual prosthetic elements) which can also arise even if the individual preparations are sufficiently correct in themselves.

From the preceding considerations it will be apparent that only an expert dentist can achieve a correct preparation for a prosthesis without risks and uncertainties; even in the best cases the required working times are however rather long, and the operation is rather onerous from the psychological and physical point of view for the dentist, and tiresome for the patient.

The object of the present invention is to provide a support and guide apparatus for a dental drill, which allows the disadvantages associated with known and above specified prosthesis preparation techniques to be overcome.

The said object is achieved by the present invention in that it relates to a support and guide apparatus for a dental drill of the type including a pneumatically driven turbine which can rotate about its own axis and rotatably drive a milling cutter, characterised in that it includes a movable arm which can be secured to fixed support means, provided with attachment means for the tail of the said drill, the said arm including restraint means operable to maintain the said axis of rotation of the said turbine orthogonal to a predetermined working plane.

The present invention further includes an apparatus for stabilizing the patient's head and jaw, particularly for dental use.

Dental chairs are known in the art, these comprising substantially a seat, a seat back and a headrest disposed on an upper portion of the seat back; such chairs are generally provided with means for adjustment of the inclination of the seat back and possibly also the seat, to allow the optimum disposition of the patient from the point of view of the patient's comfort and the operating convenience of the dentist.

In the said chairs, the headrest forms a more or less effective rear support for the head but certainly is insufficient to prevent even involuntary movements of the head during the dental work. Moreover, the position of the patient's jaw during the dental work is determined by the muscular force of the patient and is not subject to any external constraints; therefore small movements or tremors of the jaw frequently occur.

The instability of the head and jaw is, as is obvious, dangerous in any type of dental work, but is particularly so during work which requires the dentist to use a turbine drill, in which case it can give rise to imperfections in the work (for example in the preparation for prostheses in which the satisfactory result of the work is tied to the observance of very tight geometric tolerances) or, in extreme cases to injury to the patient's gums or cheeks. Another object of the present invention is to provide an apparatus for stabilizing the patient's head and jaw which, when fitted to a dentist's chair, makes it possible to overcome the above explained difficulties.

For a better understanding of the present invention a preferred embodiment will be described hereinafter purely by way of non-limitative example and with reference to the attached drawings, in which:

FIG. 6 is a section taken on the line VI—VI of FIG. 1;

FIG. 5 is a section taken on the line IX—IX of FIG. 8;

FIG. 10 is a section taken on the line X—X of FIG. 6;

FIG. 11 is a partially sectioned side view of the head and jaw stabilisation apparatus illustrated in FIG. 1;

FIG. 12 is a partial plan view of a variant of a detail of FIG. 1; and

FIG. 13 is a section taken on the line XIII—XIII of the detail of FIG. 12.

Figure 1:
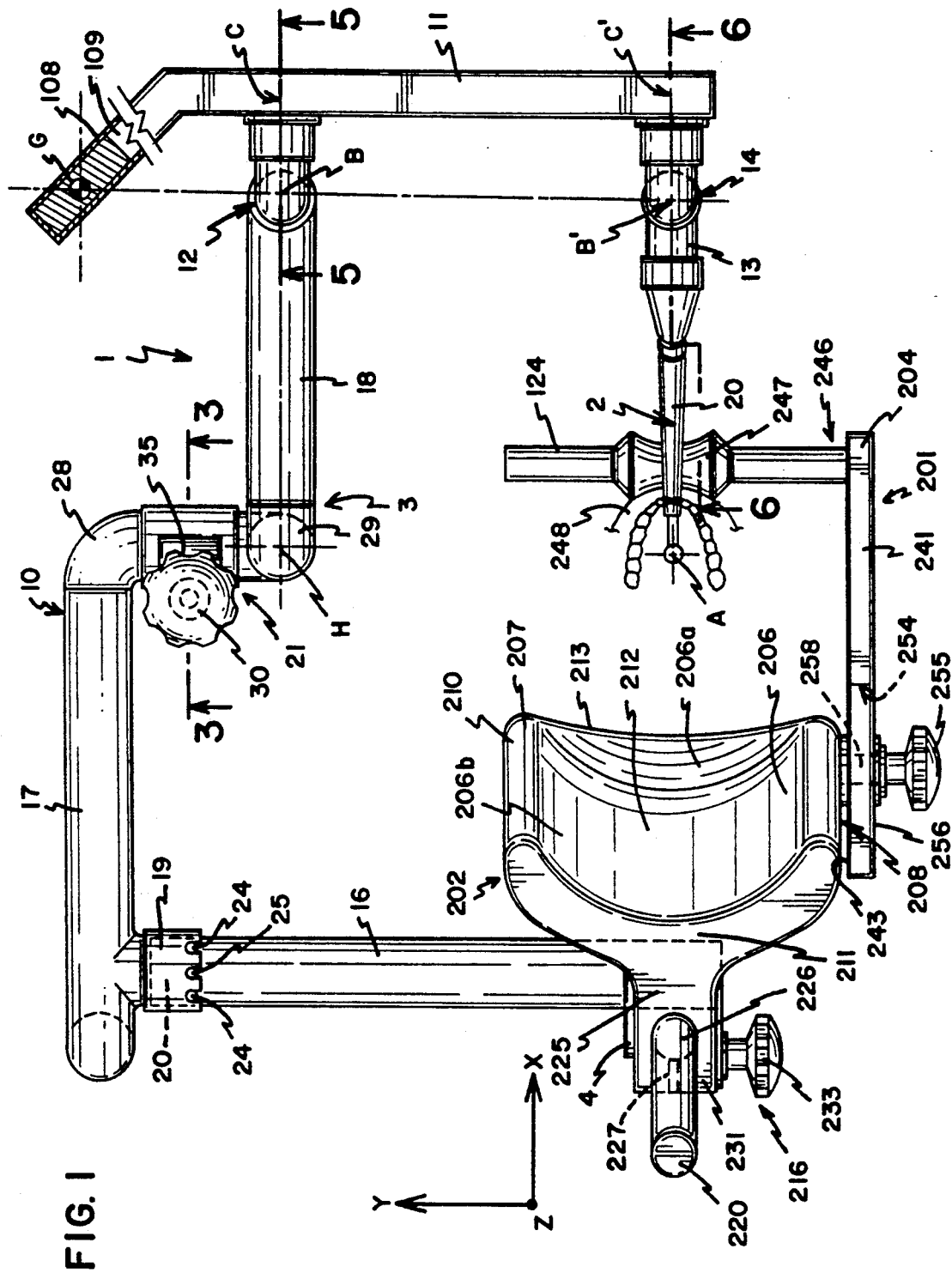
FIG. 1 is a plan view from above of a support and guide apparatus for a dental drill, with an apparatus for stabilising the head and jaw, formed according to the principles of the present invention.
Figure 2:
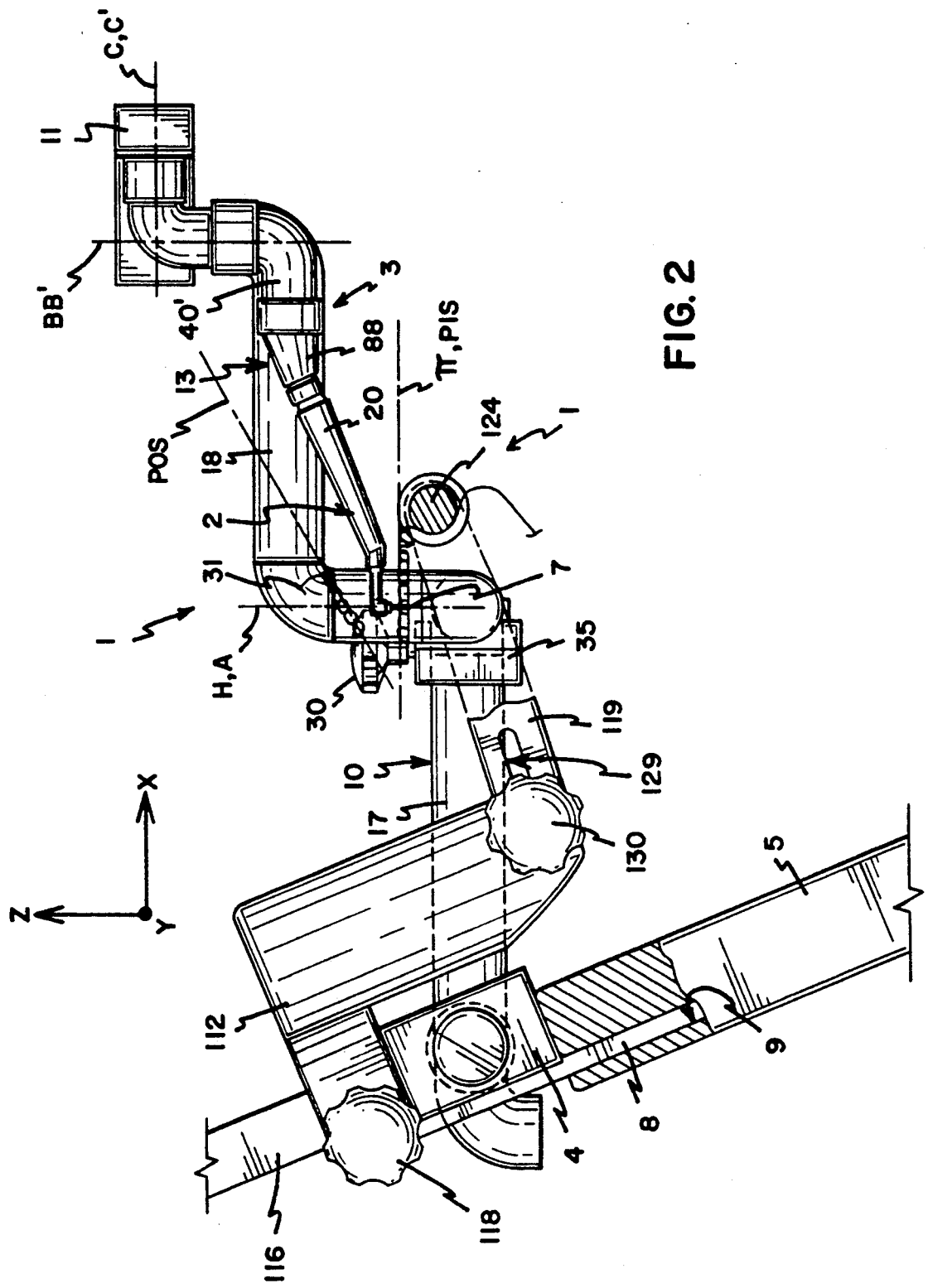
FIG. 2 is a side view of the apparatus of FIG. 1.

With reference to FIGS. 1 and 2, support and guide apparatus 2 for dental use is generally indicated with reference numeral 1.

The apparatus 1 essentially comprises an articulated arm 3 which is adapted to be fixed so as to project from a support 4 secured to an upper portion of a seat back 5 of a dentist's chair, partially illustrated in FIG. 2.

The support 4 can conveniently be constituted by a metal block of rectangular form, from a lower face of which extends a prong 8 which can be inserted into a corresponding socket 9 in the seat back 5 and locked therein, for example by means of a clamping screw not illustrated. The drill 2 is provided, in a known way, with a high speed turbine, not illustrated, which is driven to rotate by compressed air delivered to the drill itself by means of a tube 6 partially illustrated in broken outline in FIG. 6. The turbine carries a spindle on which various tools can be mounted; in particular, in FIG. 2 there is shown a milling cutter 7 the axis of rotation of which is indicated A.

The arm 3 can carry the drill 2 at its free end and is composed of several portions joined together, as will be described in detail hereinbelow, to permit guided manual displacement of the drill itself in such a way that the axis A of the milling cutter is maintained always parallel to itself and orthogonal to a predetermined working plane $\pi$. Conveniently the attitude of the chair and the arm 3 are adjusted in such a way that the plane $\pi$ coincides with an occlusal plane of the patient as illustrated in FIG. 2.

The arm 3 includes a first portion 10 which is fixed in use, but which is provided with adjustment means for preliminarily determining its geometry, which projects forwardly and laterally (with respect to the position of the patient on the chair) from the said support 4, an intermediate portion 11 articulated to a free end of the first portion 10 by first ball-joint means 12 and extending transversely of the chair, above it and towards the patient, and a terminal portion 13 articulated to one end of the intermediate portion 11 by second ball-joint means 14. The terminal portion 13 of the arm 3 is provided with attachment means for a tail 20 of the drill 2.

The structure of the arm 3 will be described in detail below. For convenience of reference the spatial arrangement of various elements is referred to a set of three axes X,Y and Z illustrated in FIGS. 1 and 2, respectively identifying a longitudinal direction, a transverse direction and a vertical direction with respect to the chair. Hereinafter references to these axes has no limitative function but are used solely for clarity of explanation.

The first portion 10 is essentially constituted by a tube 16 having an axis parallel to the Y axis and projecting from one side of the support 4, and by two tubular elements 17, 18 parallel to the X-Z plane and connected together by means 21 for adjusting their relative inclination; the tubular element 18 is conveniently disposed higher and closer to the longitudinal centre line of the chair than the tubular element 17.

The tubular element 17 is integrally provided with a laterally projecting sleeve 19 which is engaged on a free end of the tube 16, defining with it a friction coupling 22. The sleeve 19 is provided with a plurality of frontal slots 24 engageable selectively by a radial pin 25 carried by the end of the tube 16 in such a way as to provide a plurality of stable angular positions of the tubular element 17 in the X-Z plane. In particular, in the illustrated embodiment there are provided three slots 24 at 30° to one another with the central one of these corresponding, in the particular position of the seat back 5 as illustrated, to the horizontal position of the tubular element 17 illustrated in the drawings.

Figure 3:
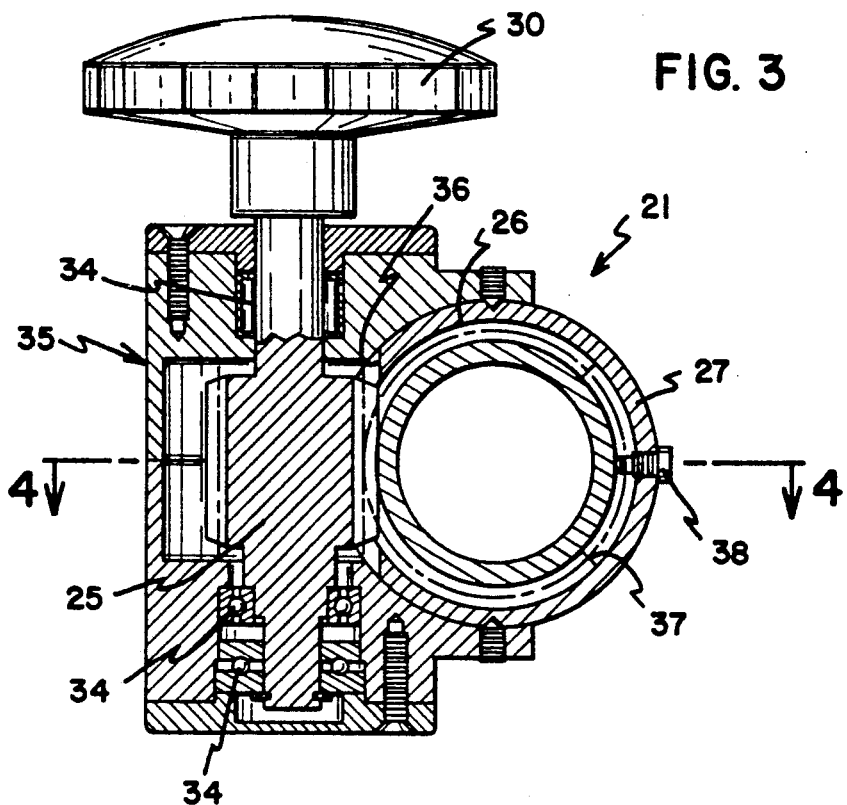
FIG. 3 is a section taken on the line III—III of FIG. 1.
Figure 4:
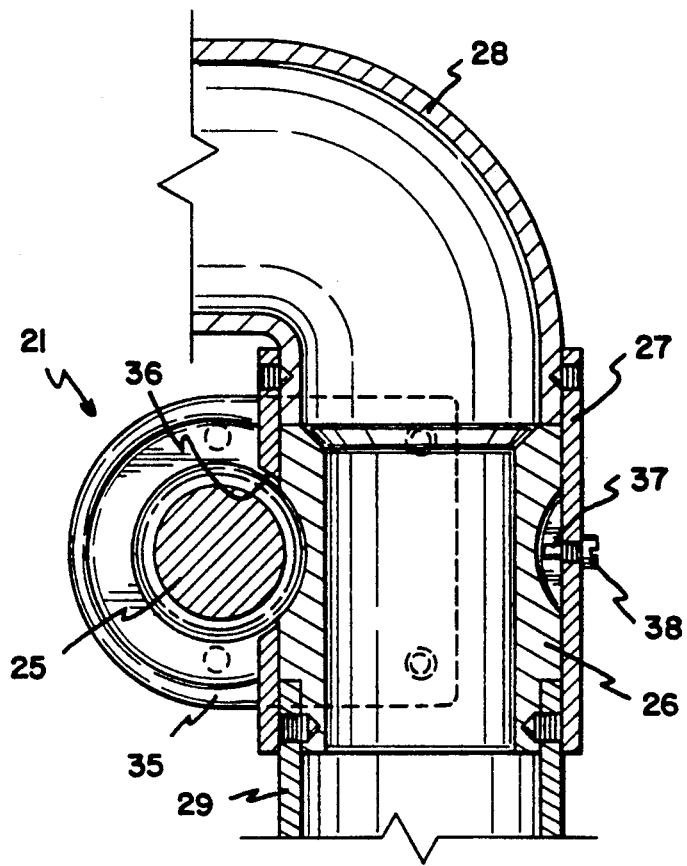
FIG. 4 is a section taken on the line IV—IV of FIG. 3.

The said adjustment means 21 illustrated in detail in FIGS. 3 and 4 essentially comprise a worm screw transmission system having a worm screw (25) and a helical gear wheel (26). The wheel 26 is hollow and housed freely rotatably within a cylindrical bush 27 the axis of which is parallel to the Y axis, and which is rigidly fixed to the tubular element 17 by an elbow connector 28. The gear wheel 26 is in turn connected to the tubular element 18 by a double elbow tubular connector 29 conveniently constituted by two elbow portions 31, 32 respectively fixed to the gear wheel 26 and to the tubular element 18, which are frictionally coupled together with the possibility of relative rotation about an axis H orthogonal to the axes of the gear wheel 26 and the tubular element 18.

The screw 25 can be turned by means of an end handle 30 and is rotatably supported, by means of bearings 34, within a casing 35 rigidly fixed on one side of the bush 27. This latter is provided with a tangential opening 36 to allow meshing of the screw 25 with the gear wheel 26. As is clearly visible in FIG. 3 the screw is provided with a circumferential groove 37 of predetermined angular width, for example 90°, which is engaged by a screw 38 screwed into the wall of the portion 27 to limit the angular movement of the gear wheel itself. In the illustrated example this movement can be ±45° with respect to the intermediate position illustrated in which the tubular elements 17 and 18 are parallel to one another.

Figure 5:
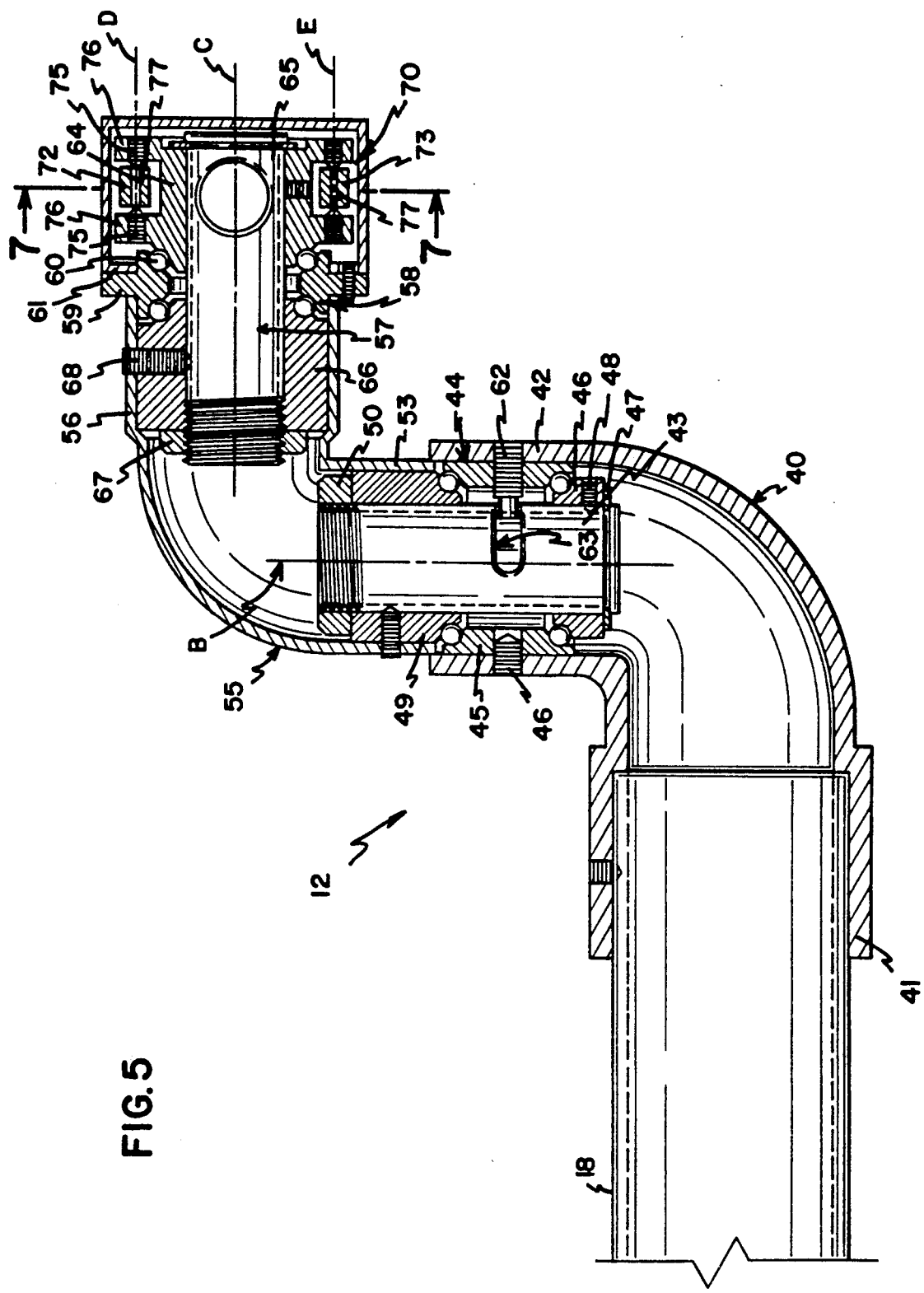
FIG. 5 is a section taken on the line V—V of FIG. 1

FIG. 5 illustrates in detail the pivot coupling means 12 for connection of the intermediate portion 11 of the arm 3 to the tubular element 18.

These pivot coupling means comprise a first elbow coupling 40 which is rigidly fixed by its portion 41 to the free end of the tubular element 8 and has a second portion 42 facing upwardly with an axis B orthogonal to that of the first and parallel to the X-Z plane. A hollow cylindrical pin 43 coaxial with the portion 42 and housed at least partly therein is supported for free angular movement and axially fixed by a thrust bearing 44 having two rings of obliquely contacting balls.

A central ring 45 of the bearing 44 is centred in the portion 42 and is fixed rigidly to it by a radial grub screw 46; the ring 45 is clamped, with the interposition of respective rings of balls, between a lower ring 46 fixed to the pin 43 by a circlip 47 and a radial grub screw 48, and an upper ring 49 on which acts a ring nut 50 screwed on one end of the pin 43 and operable to adjust the bearing clearances.

The upper ring is in turn fixed within a first portion 53 of a further elbow coupling 55, which includes a second portion 56 having an axis C orthogonal to the axis B.

The rotation of the pin 43 with respect to the portion 42 is limited, conveniently to ±90° with respect to the illustrated position in which the second portion 56 of the coupling 55 is disposed in the opposite direction from the tubular element 18 and the axis C is parallel to the axis of the element 18, by a radial grub screw 62 fixed to the central ring 45 and engaging a circumferential groove 63 in the pin 43.

The intermediate portion 11 of the arm 3, which has a hollow rectangular section, is supported rotatably on a hollow pin 57 on the axis C, fixed to the second portion 56 of the connector 55. More particularly, the portion 11 is mounted on a bearing 58 having two rings of obliquely contacting balls, which essentially comprises a central ring 59 shaped as a flange and fixed in an aperture 60 in a side wall 61 of the portion 11, a first lateral ring integrally defined by a wheel 64 fitted on one end 65 of the pin 57 within the portion 11, and a second lateral ring 66 fitted on an opposite end of the pin 57 within the connector 55 and clamped by a ring nut 67. A second ring 66 and the pin 57 are locked angularly in the portion 56 of the connector 55 by a radial grub screw 68; the wheel 64 is therefore also angularly fixed.

The portion 11 is thus free to rotate together with the central ring 59 about the axis C of the pin 57. The P C means 14 between the intermediate portion 11 and the terminal portion of the arm 3 are illustrated in detail in FIG. 6. These pivot coupling means are entirely analogous to the means 12 described, and are therefore described hereinafter in summary, utilising the same reference numerals for the same or corresponding elements of the pivot coupling means 12 with the addition of an apostrophe (').

The P C means 14 comprise a first pin 37' having an axis C' parallel to the axis C, which is mounted on a bearing 58' rotatably with respect to an opposite end of the intermediate portion 11. On one end of the pin 57' within the intermediate portion there is rigidly fixed, in a manner not illustrated, a wheel 64' corresponding to the wheel 64, which constitutes a lateral ring of the bearing 58'. On the other lateral ring 66' of the bearing 58' is mounted a first portion 56' of an elbow connector 55' a second portion 53' of which fixedly carries a pin 43' having an axis B' parallel to the axis B. A further elbow connector 40' is mounted by its end 42' on the pin 43' by means of a bearing 44'.

A free end 41' of the connector 40', having an axis F orthogonal to the axis B' and rotatable with respect to this latter, is connected to the terminal portion of the arm 3 in the manner described below.

As has been mentioned above, the axis B' is parallel to the axis B. So that this condition, which is essential for the present invention, is maintained when the portions 10, 11 and 13 of the arm 3 turn about the axis C and C', auxiliary restraint means are provided according to the invention, which have the purpose of preventing a rotation of the pin 57' during rotations of the intermediate portion about the axis C. These restraint means are constituted in particular by an articulated parallelogram device housed in the intermediate portion 11 itself, two embodiments of which are illustrated respectively in FIGS. 5, 6 and 7 and FIGS. 8 an 9.

Figure 7:
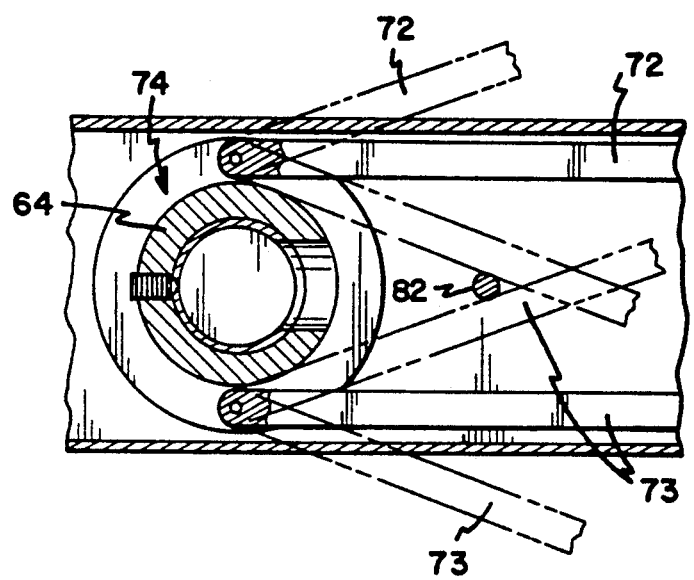
FIG. 7 is a section taken on the line VII—VII of FIG. 5.

With reference to FIGS. 5, 6 and 7, the device 70 comprises a pair of parallel rods 72, 73 pivoted at their ends to the wheels 64 and 64'. The ends of the rod 72 are pivoted to the wheels 64, 64' about respective axes D, D' parallel to but eccentric with respect to the axes C and C' respectively; the ends of the rod 73 are pivoted to the wheels 64, 64' about respective axes E, E', which are parallel to and diametrically opposite the axes D, D' with respect to the axes C, C' respectively.

The wheels 64, 64' thus define the other two sides of the articulated parallelogram.

From this arrangement it follows that, the wheel 64 being angularly fixed, the wheel 64' also is maintained angularly fixed during rotations of the intermediate portions 11 and with it the axis B'.

From a constructional point of view the wheels 64, 64' are conveniently formed with respective grooves 74, 74' which house the ends of the rods 72, 73.

The axes D, E (D' E') are conveniently defined by pairs of grub screws 75 (75') screwed into the walls 76 (76) of the wheel 64 (64') axially delimiting the above mentioned groove 74 (74') and cooperating with respective holes 77 (77') of the rods 72, 73.

Figure 8:
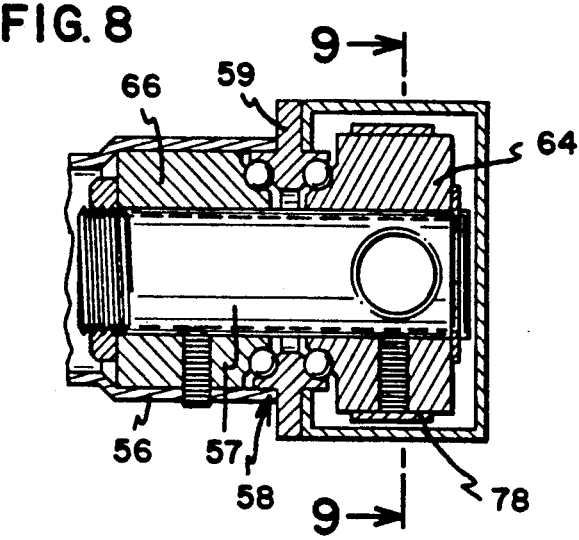
FIG. 8 is a section similar to that of FIG. 5 illustrating a variant of a detail of FIG. 5.
Figure 9:
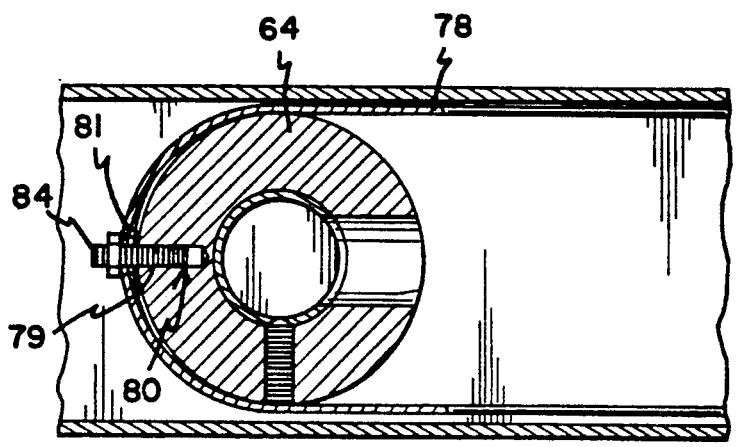

As is clearly visible in FIG. 7, within the intermediate portion 11 there are conveniently provided one or more stop pins 82 for the purpose of limiting the angular excursion of the rods 72 and 73, and therefore of the portion 11 itself In the variant illustrated in FIGS. 8 and 9, the wheels 64, 64' are constituted by respective pulleys over which passes a belt 78 which is locked at least at one point with respect to the pulleys themselves to prevent relative sliding. In particular, FIG. 9 shows the connection of the belt 78 to the pulley 64 by means of a screw 79 disposed in a hole passing through the belt and screwed into a radial hole 80 on the periphery of the pulley 64. The belt is conveniently clamped between a saddle 81 fixed to the screw, and a nut 84 which is screwed onto the screw; by screwing and unscrewing the screw an adjustment of the tension in the belt 78 is achieved.

With this arrangement an articulated substantially parallelogram arrangement is again achieved in which the sides are constituted by the free runs of the belts 78 and the conjunction of the end points of the sections of the belts 78 passing over the respective pulleys 64, 64'.

In FIG. 6 the terminal portion 13 of the arm 3 and the connections of this portion to the connector 40' and the drill 2 are also illustrated in detail. The portion 13 includes a tubular pin 85 on one end of which an attachment element 88 for the drill 2 is rigidly fixed. This attachment element has an internal cavity formed by two cylindrical sections 99 inclined to one another and constituting respective sockets for the tubular pin 85 and for the tail 20 of the drill 2. The portion 13 further includes a bush 94 rotatably mounted on pin 85 and clamped against the attachment element 88 by a ring nut 95. The bush 94 is angularly and axially fixed in the free end 41' of the elbow connector 40'; therefore the pin 85 and the attachment element 88 fixedly connected to it can turn about the axis F. This possibility of rotation is limited by a radial grub screw 96 which also locks the bush 94 in relation to the elbow connector 40', which extends inwardly of the bush itself and slidably engages a circumferential groove 97 in the pin 85.

Finally there are provided frontal engagement means between the attachment element 88 and the bush 94 for locking these in relation to one another in a plurality of preferential angular positions.

These engagement means are constituted by a ball 98 slidably mounted in an axial hole 99 of the element 88 and thrust by a spring 100 housed in the same hole against a frontal surface 103 of the bush 94, which is provided, as illustrated in detail in FIG. 10, with a plurality of suitably angularly spaced indentations 104, 105 and 106. In particular, the indentations 104 are diametrically opposite one another and, if engaged by the ball 98, form two main working positions of the drill 102, at 180° from one another, in which the axis A oft he milling cutter 7 is parallel to the axis B' and the milling cutter 7 is facing downwardly or upwardly; these positions are used for the preparation of tooth prostheses in the upper and lower dental arch respectively.

The indentations 105 and 106 define auxiliary positions of the drill which are useful for particular operations; these positions are turned through ±30° and ±45° with respect to each of the principle positions.

According to a further important characteristic of the present invention, the intermediate portion is provided with a counter weight 108 which balances its weight and the masses suspended from it, that is to say the pivot coupling means 14, the terminal portion 13 and the drill 2. This counterweight is lodged in an end section 109 of the portion 11 opposite that in which the pivot coupling means 14 are connected. The section 109 is conveniently turned towards the tubular element 18 in such a way that the centre of gravity G of the counter weight is located substantially on the extension of the line joining the intersection point between the axis B and C to the intersection point between the axis B' and C'. In this way the components of the weight forces are balanced both in the plane identified by the axes B and B' and in the plane identified by the axes C and C'. These latter are zero in the working position illustrated, but it is evident that they arise when the working plane $\pi$ is not horizontal. Since friction and other operating parameters (wear, dimensional tolerances etc) which are difficult to predict beforehand can alter the theoretical balance conditions described, the counterweight is conveniently housed slidably in the end section 109 of the portion 11 and can be fixed (for example by means of an adjustment screw) in a correct position determined experimentally during calibration of the apparatus.

Finally, the apparatus is conveniently provided with a device for stabilisation of the head and jaw of the patient, generally indicated with the reference numeral 201.

This apparatus essentially comprises a headrest 202 which in use is adapted to constitute a rear support for the head 203 of a patient, partially illustrated, and means 204 for locking the patient's jaw 205 in an open position.

The headrest 202 is shaped in such a way as to define three contact zones 206a, 206b, 206c with the patient's head 203; the zones 206a, 206b, 206c are not aligned, so that, in use, the position of the head is stable and uniquely determined. More particulary, the zone 206a is intended to receive and support a portion of the nape of the patient's neck whilst the two zones 206b and 206c are intended to support two symmetrical portions of respective occipital zones of the patient's head.

The overall shape of the headrest 202 includes hollow, approximately cylindrical sectors on the side which in use cooperates with the patient's head, and substantially comprises two curved side walls 207 and 208 integrally connected and joined to a central wall 211. The side walls 207, 208 are frontally delimited by a substantially rectilinear edge 210. The central wall 211 has a curved lower portion 212 projecting forwardly, which joins the side walls 207 and 208 and terminates with a slightly concave lower edge 213.

As is clearly illustrated in FIG. 1, the three support zones mentioned above are located respectively close to the edge 213 of the lower portion 212 (zone 206a) and in the connection zones between the central wall 211 and the side walls 207, 208 (zones 206b and 206c).

The headrest 202 is conveniently constituted (FIG. 11) by a metal body 214, a layer of padding material 215, such as, for example, foam rubber, positioned in contact with the body 214 on the side of this which in use faces towards the patient's head, and a covering 217 of leather, artificial leather or any suitable synthetic material.

The headrest 202 is further provided with fixing means 217 for fixing it in an adjustable position to the seat back 5 of a dentist's chair which is partially illustrated.

These means 216 comprise the support 4 of prismatic form from which extend, respectively upwardly and downwardly, a circular section bar 220 on which the headrest 202 is mounted, and a rectangular section prong 221 engagable in a corresponding socket 222 formed in the seat back itself and locked in position, for example, by means of screws not illustrated.

The metal body 214 of the headrest 202 includes a rear projection 225 which has a through hole 226 slidably housing the bar 220 and a through slot 227 along the rear generatrix of the said hole, which sub-divides the projection 225 into two symmetrical portions 231 and 232.

The fixing means 216 include a threaded pin 230 which passes transversely, perpendicularly of the axis of the hole 226, through the two portions 231 and 232 and is angular fixed with respect to the portion 232, and a handle 233 provided with a threaded axial hole, also not visible in the drawing. In use, by screwing or unscrewing the handle 233 on the said pin, release or respectively, clamping of the portions 231 and 232 onto the bar 220 is achieved; it is therefore possible to adjust the position of the headrest 202 along the bar 220 between a lower limit position (illustrated in the drawing) in which the projection 225 cooperates with the support 4, and an upper limit position (partially illustrated in broken outline in FIG. 11) beyond which separation of the headrest 202 from the bar itself would occur.

According to the present invention the means 203 for locking the patient's jaw are essentially constituted by a bracket 241 fixable so as to project forwardly of an external flank 243 of the side wall 208 of the headrest 202, and by a transverse patient's jaw locking element 246 carried fixedly by the bracket 241.

The transverse locking element 246 is of elongate cylindrical form and is disposed in use facing the headrest 202 and provided with a support element 247 conveniently of soft material, which can be brought into contact with an upper frontal zone 248 of the patient's chin 251 to lock the patient's jaw in the open position as illustrated in FIG. 11.

This engagement element has a shape which is a solid of revolution with a concave curvilinear generatrix, and is disposed coaxially of the locking element 246.

The bracket 241 is provided at its end 242 with a longitudinal slot 254 operable in use to house a respective threaded pin 258 fixed rigidly to the headrest 202 on the side face 243 of the headrest 202 itself; on the pin is screwed a handle 255 provided with a corresponding threaded hole, the handle being able to press against an outer lateral surface 256 of the bracket 251 to lock this latter, and therefore the locking element 246 and the abutment element 247 fixed to it, in the desired position.

The projection and inclination of the bracket 241 can therefore be adjusted by releasing the handle 255 in dependence on the patient's anthropometric characteristics and the working requirements of the dentist.

It is to be noted that the slot 254 is open towards the end of the bracket 241 in such a way as to permit the removal of the bracket itself without unscrewing the handle 255 completely. FIGS. 12 and 13 illustrate an alternative embodiment of the engagement element 247 in which this element is delimited frontally and upwardly by two flat orthogonal surfaces 260 which are joined together and which lie on respective planes tangential to the outer surface of the locking element 246.

The operation of the apparatus 1 is as follows.

After the patient has taken his position on the chair, the seat back 5 of which can be more or less inclined according to the custom or operating requirements of the dentist, the position of the head and jaw is fixed by means of the device 201.

The working plane $\pi$ is thus defined, which for a prosthesis preparation operation coincides with the lower occlusal plane POI (as illustrated in FIG. 2) or the upper occlusal plane (POS).

FIG. 2 illustrates the case in which the seat back 5 of the seat is inclined in such a way that the plane $\pi$ is horizontal; obviously this condition is not essential in that the working position can be chosen by the dentist.

Having defined the working plane $\pi$ it is necessary suitable to adjust the position of the first portion 10 of the arm so that the axes B, B' and therefore A are perpendicular to this plane. This is achieved by selecting the most convenient position of the friction coupling 22 and then acting on the handle 30 for a fine adjustment of the inclination of the tubular element 18.

To improve visibility during work it can be convenient suitably to orientate the tubular element 18 by rotating it with respect to the tubular element 17 about the axis H; the friction coupling between the portions 31 and 32 of the connector 29 ensure the stability of the relative position selected.

After the described initial adjustment operations of the apparatus have been performed the drill 2 is guided by the arm 3 by the effect of the device 70 described hereinabove, to translate whilst maintaining the axis A of the milling cutter always parallel to itself and orthogonal to the plane $\pi$.

The displacement of the drill along the plane $\pi$ is made possible by the composition of the rotations about the axis B and B'; displacement in a direction orthogonal to the plane $\pi$ is permitted by the composition of the rotations about the axes C and C'.

The attachment element 88 can moreover rotate about the axis F, and the ball coupling (98) allows the desired orientation of the milling cutter axis to be achieved rapidly and with high precision.

In particular, when working on a tooth of the upper dental arch the attachment element 88 is conveniently turned through 180° with respect to the position illustrated in FIG. 2, and the working plane $\pi$ coincides with patient's upper occlusal plane.

The described arrangement of the counterweight 108 ensures that the movable masses of the arm 3 and the drill are in a balance condition in all attitudes of the arm 3.

From the above the advantages which can be obtained with the present invention are evident.

Above all the apparatus 1 ensures that the axis A of the milling cutter is maintained parallel to itself and orthogonal to the working plane $\pi$ during displacements of the drill which are imposed manually by the operator. The dentist can therefore perform the prosthesis preparation operations with high precision, in particular obtaining the optimum cone angle of the stump, much more quickly than can be obtained with traditional "freehand" techniques. Moreover, if the preparation involves several teeth intended to constitute the supports for a single prosthesis the insertion axis prepared on each tooth is rigorously parallel to the others.

Another important advantage associated with the present invention derives from the static balance of the movable masses the consequence of which is that the dentist can manoeuvre the drill in any way substantially free from weight.

Moreover, the device 201 stabilises the position of the patient's head and jaw; the cause of errors or even of accidental injuries due to movements of the patient or by contact of the drill with the teeth of the opposite dental arch consequent on involuntary closure of the mouth due to fatigue of the muscles is therefore also overcome. Finally, it is clear that the apparatus 1 can have modifications and variations introduced thereto which do not depart from the protective ambit of the present invention.

In particular, the arm 3 can be made in any way and with any number of parts, and the device 70 can be replaced by any other device operating equivalently. Moreover, servo actuators for control of the relative movements of the various parts could be employed.

Additionally, in a possible alternative embodiment not illustrated in the drawings, the bracket 241 could be provided with a second support bracket fixed on the other side of the headrest 202 in order better to support the transverse locking element 246 and, as a result, the patient's jaw.

Finally, in a further embodiment of the invention, not illustrated in the drawings, the patient's jaw locking means could be constituted by a belt also fixable to the sides of the headrest 202; the belt would then be provided with adjustment elements for varying its length such as for example, buckles, as well as an engagement element substantially equivalent to the element 247.

I claim:

1. Support and guide apparatus for a dental drill of the type comprising a pneumatically driven turbine rotatable about its own axis and operable to drive a milling cutter, said apparatus comprising a movable arm which can be attached to fixed support means and provided with attachment means for a tail of said drill, said arm including restraint means operable to maintain said axis of rotation of said turbine orthogonal to a predetermined working plane, the apparatus further comprising means for stabilizing a head and a jaw of a patient, particularly for dental use, comprising a headrest which can be fixed to a chair to constitute a rear support for a patient's head, and means for locking the patient's jaw with respect to said headrest in a jaw-open position.

2. Support and guide apparatus according to claim 1, wherein said locking means are attached to said headrest and include at least one engagement element cooperable with an upper frontal portion of a patient's chin.

3. Support and guide apparatus according to claim 2, further comprising at least one bracket fixable to one side of said headrest, said bracket projecting towards a forward part of said headrest and carrying a transverse element for locking said jaw of the patient.

4. Support and guide apparatus according to claim 3, wherein said bracket is provided at one end with a through slot engageable slidably by means for locking said bracket on said headrest.

5. Support and guide apparatus according to claim 4, wherein said locking means include a threaded pin projecting from said side of said headrest, engageable in said slot of said bracket, and a threaded handle on said pin and cooperable under pressure with a lateral surface of said bracket.

6. Support and guide apparatus according to claim 2, wherein said at least one engagement element is carried by said transverse element for locking said jaw.

7. Support and guide apparatus according to claim 2, wherein said engagement element has a form comprising a solid of rotation with concave curvilinear generatrix.

8. Support and guide apparatus according to claim 1, wherein said headrest defines at least three contact zones with the patient's head, which zones are not aligned with one another.

9. Support and guide apparatus according to claim 1, wherein said headrest has a shape of a semi-cylindrical sector with a pair of side walls joined to a central wall; said central wall including a curved lower portion projecting forwardly and terminating with a slightly concave lower edge, and joined to said side walls.

10. Support and guide apparatus according to claim 1, wherein said headrest has respective fixing means adjustable with respect to a respective seat back of a dentist's chair.

11. Support and guide apparatus for a dental drill of the type comprising a pneumatically driven turbine rotatable about its own axis and operable to drive a milling, said apparatus comprising cutter a movable arm which can be attached to fixed support means and provided with attachment means for a tail of said drill, said arm including restraint means operable to maintain said axis of rotation of said turbine orthogonal to a predetermined working plane, said arm including a first portion which can be attached to said fixed support means, an end terminal portion provided with said attachment means for said drill, and an intermediate portion, said first portion and said end portion of said arm being articulated to said intermediate portion by means of first and second pivot coupling means operable to permit relative rotation about respective first axes parallel to one another and orthogonal to said working plane, at least one of said portions being rotatable about at least one another axis parallel to said working plane, said restraint means including an articulated parallelogram device, said pivot coupling means each defining a respective second axis of relative rotation parallel to one another and to the said working plane between said first portion and said intermediate portion and between said intermediate portion and said end portion, said intermediate portion extending orthogonally with respect to said second axes, said apparatus further including counterweight means for balancing said arm, wherein said articulated parallelogram device includes a pair of wheels coaxial with said second axes of said pivot coupling means, one of which is angularly fixed, and a pair of rods parallel to one another and pivoted at their respective ends to respective diametrically opposite points of said wheels.

* * * * *